United States Patent
Datta et al.

(10) Patent No.: US 10,058,382 B2
(45) Date of Patent: Aug. 28, 2018

(54) CATHETER WITH PROTECTIVE BARRIER MEMBER

(75) Inventors: Keshava Datta, Chino Hills, CA (US); Jeffrey W. Schultz, Chino, CA (US)

(73) Assignee: Biosense Webster, Inc., Irvine, CA (US)

( * ) Notice: Subject to any disclaimer, the term of this patent is extended or adjusted under 35 U.S.C. 154(b) by 358 days.

(21) Appl. No.: 12/346,827

(22) Filed: Dec. 30, 2008

(65) Prior Publication Data

US 2010/0168676 A1 Jul. 1, 2010

(51) Int. Cl.
*A61N 1/05* (2006.01)
*A61B 18/14* (2006.01)
*A61B 18/12* (2006.01)
*A61N 1/08* (2006.01)

(52) U.S. Cl.
CPC ...... *A61B 18/1492* (2013.01); *A61B 18/1233* (2013.01); *A61N 1/0517* (2013.01); *A61N 1/08* (2013.01)

(58) Field of Classification Search
CPC ........ A61B 18/1492; A61B 2018/0016; A61B 2018/0022; A61B 2018/00232; A61N 1/0517; A61N 1/0519; A61N 1/08
USPC .............. 607/124, 133, 134; 604/96.01, 104, 604/95.04, 103.06, 103.07, 103.14
See application file for complete search history.

(56) References Cited

U.S. PATENT DOCUMENTS

| | | |
|---|---|---|
| 4,898,591 A | 2/1990 | Jang et al. |
| 5,104,393 A | 4/1992 | Isner et al. |
| 5,391,199 A | 2/1995 | Ben-Haim |
| 5,427,119 A | 6/1995 | Swartz et al. |
| 5,443,489 A | 8/1995 | Ben-Haim |
| 5,480,422 A | 1/1996 | Ben-Haim |
| 5,487,385 A | 1/1996 | Avitall |
| 5,497,774 A | 3/1996 | Swartz et al. |
| 5,546,951 A | 8/1996 | Ben-Haim |
| 5,558,091 A | 9/1996 | Acker et al. |
| 5,564,440 A | 10/1996 | Swartz et al. |
| 5,575,766 A | 11/1996 | Swartz et al. |
| 5,582,609 A | 12/1996 | Swanson |

(Continued)

FOREIGN PATENT DOCUMENTS

WO    WO 93/20767    10/1993

*Primary Examiner* — Tammie K Marlen
(74) *Attorney, Agent, or Firm* — Lewis Roca Rothgerber Christie LLP (57) ABSTRACT

A device that shields internal organs and tissues from medical procedures performed within a patient's body, especially in the chest cavity where ablation and related procedures are performed in or near the heart, includes a catheter body, a distal section, and a barrier member that can be inflated with fluid to act as a barrier to extreme temperatures and physical trauma, and be deflated to a smaller size to facilitate entry and removal from the patient's chest cavity. In a more detailed embodiment, the barrier member is a balloon that can protect the esophagus, which can be provided with folds and shape memory elements so that the balloon expands and collapses into predetermined configurations. Fluid is fed to and drawn from the barrier member via an irrigation tubing that extends along a catheter shaft and is in communication with a lumen of a deflectable tubing section that extends through an interior cavity of the barrier member. The catheter can be adapted for uni- or bi-directional deflection.

23 Claims, 11 Drawing Sheets

(56) References Cited

U.S. PATENT DOCUMENTS

| | | | |
|---|---|---|---|
| 5,617,854 A | | 4/1997 | Munsif |
| 5,827,289 A | * | 10/1998 | Reiley .................. A61B 10/025 606/191 |
| 6,004,269 A | * | 12/1999 | Crowley et al. .............. 600/439 |
| 6,123,699 A | | 9/2000 | Webster, Jr. |
| 6,171,277 B1 | | 1/2001 | Ponzi |
| 6,183,463 B1 | | 2/2001 | Webster, Jr. |
| 6,198,974 B1 | | 3/2001 | Webster, Jr. |
| 6,468,260 B1 | | 10/2002 | Bunbalough et al. |
| 6,522,933 B2 | | 2/2003 | Nguyen |
| 6,689,062 B1 | | 2/2004 | Messallum |
| 7,043,307 B1 | * | 5/2006 | Zelickson et al. ............ 607/101 |
| 7,083,614 B2 | | 8/2006 | Fjield et al. |
| 7,112,172 B2 | | 9/2006 | Orban, III et al. |
| 7,762,261 B1 | * | 7/2010 | Fortuna .................... 128/207.14 |
| 2006/0118127 A1 | | 6/2006 | Chinn |
| 2007/0112300 A1 | * | 5/2007 | Roman et al. ........... 604/103.07 |
| 2008/0125708 A1 | * | 5/2008 | Feng .......................... 604/96.01 |
| 2008/0161890 A1 | * | 7/2008 | Lafontaine .................... 607/105 |
| 2009/0299327 A1 | * | 12/2009 | Tilson et al. ................. 604/500 |

\* cited by examiner

CATHETER WITH PROTECTIVE BARRIER MEMBER

FIELD OF INVENTION

This invention is directed to a device that shields internal organs and tissues from medical procedures performed within a patient's body, in particular, a catheter that protects organs and tissues from ablation and other electrophysiologic procedures conducted in or near the heart.

BACKGROUND OF INVENTION

Cardiac arrythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reenetrant type, cardiac arrhythmias may also have a focal origin, such as when an isolated region of tissue in an atrium fires autonomously in a rapid, repetitive fashion.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Catheter ablation procedures treat atrial fibrillation through cardiac tissue ablation. Examples of catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang, et al., U.S. Pat. No. 5,487,385 to Avitall, and U.S. Pat. No. 5,582,609 to Swanson, the disclosures of which are incorporated herein by reference. The use of particular guiding sheath designs for use in ablation procedures in both the right and left atrial chambers are disclosed in U.S. Pat. Nos. 5,427,119, 5,497,774, 5,564,440 and 5,575,766 to Swartz et al., the entire disclosures of which are incorporated herein by reference. In addition, various energy delivery modalities have been disclosed for forming such atrial wall lesions, and include use of microwave, laser and more commonly, radiofrequency energies to create conduction blocks along the cardiac tissue wall, as disclosed in WO 93/20767 to Stern, et al., U.S. Pat. No. 5,104,393 to Isner, et al. and U.S. Pat. No. 5,575,766 to Swartz, et al., respectively, the entire disclosures of which are incorporated herein by reference.

The success of catheter based ablation procedures has led to numerous improvements to the catheters used for the procedures. However, the traumatic nature of the ablation procedure has given rise to certain complications. One such complication is the possibility of damaging the esophagus, which lies very close to, and often touches the outer wall of the left atrium. Damage to the esophagus is sometimes caused when the esophagus touches or is close to the tissue in the left atrium that is being ablated. The heat from the ablation procedure may penetrate through the tissue of the left atrium and reach the esophagus. This damage to the esophagus is extremely dangerous, as the damaged esophagus often becomes infected. The damage to the esophagus often manifests as a fistula, or hole, that develops over time. This hole causes any infection to spread to the heart wall. This damage carries an extremely high mortality rate. Accordingly, a need exists for a device that provides a protective shield and a physical barrier between the esophagus and the heart during ablation procedures.

SUMMARY OF THE INVENTION

The present invention is directed to a device that shields internal organs and tissues from medical procedures performed within a patient's body. The device can be a catheter having a protective shield at its distal end to protect organs and tissues from ablation and other electrophysiologic procedures conducted in or near the heart. The catheter is especially suitable to provide a physical barrier between the esophagus and the heart, in particular, the left atrium.

The device includes a catheter body, a distal section, and a barrier member that can be inflated with a fluid (e.g., carbon dioxide) to act as a protective shield for the esophagus, and deflated to a smaller size to facilitate entry and removal from the patient's chest cavity. In a more detailed embodiment, the barrier member is a balloon that can assume a polygonal or circular shape when expanded, and a folded, coiled or spiraled shape when deflated. The barrier member can be provided with folds and shape memory elements so that it expands and collapses into predetermined configuration with predetermined manners.

An intermediate section on which the barrier member is mounted can be uni- or bi-directionally deflectable. The distal section can also carry tip and ring electrodes with ablation, pacing and/or mapping capabilities. These elements as well as the barrier member can be provided with radiopaque material to provide a visual reference under X-ray or fluoroscopy. An electromagnetic position sensor may also be housed near the barrier member. A temperature sensor may also be mounted on the barrier member.

The device may incorporate a control handle with knobs and dials for a user to manipulate deflection of the tip section. The device may also be used with a trocar or a trocar in combination with a delivery device such as a guiding sheath, or with a delivery device such as a guiding sheath only. Trocars are typically used only as a port access into a patient's body.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention provides a catheter for shielding organs and/or tissues from electrophysiologic procedures performed within a patient's body, especially the chest cavity although it can adapted for use in the abdominal cavity. In particular, the catheter can be adapted to protect an esophagus by reducing the exposure of an anterior wall of the esophagus to extreme temperatures, physical penetration or trauma and/or other risks that may be posed by the procedures performed on or in the atria of the heart. In one embodiment, the catheter is adapted for (i) minimally invasive insertion into a patient's chest cavity in a collapsed configuration, (ii) expansion to a deployed configuration to shield the esophagus, and (iii) return to the collapsed configuration for repositioning or removal from the chest cavity.

Figure 1:
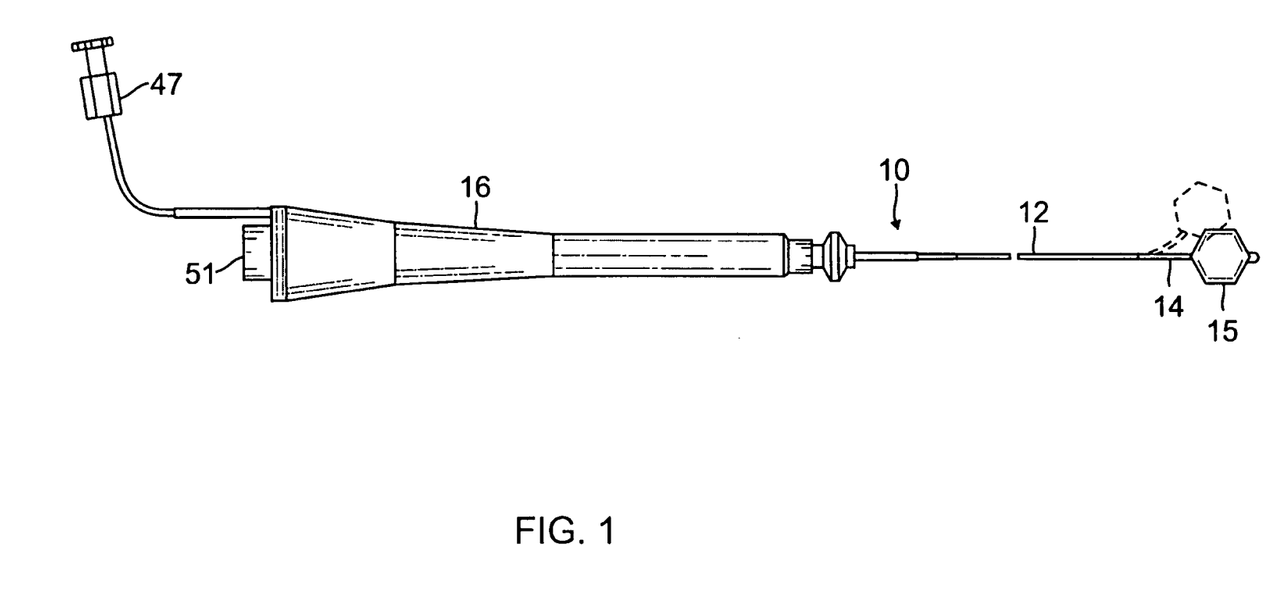
FIG. 1 is a side elevational view of an embodiment of a catheter of the present invention.

As shown in FIG. 1, one embodiment of the shielding catheter 10 generally comprises an elongated catheter body 12, a deflectable intermediate section 14 distal of the catheter body 12, and a barrier member 15 mounted on a distal end of the intermediate section 14. The illustrated embodiment of FIG. 1 also includes a control handle 16 mounted at a proximal end of the catheter body 12 adapted for a user to manipulate deflection of the intermediate section 14.

The catheter body 12 comprises an elongated tubular construction having a single central lumen 18. It will be understood, however, that the catheter body 12 may comprise more than one lumen as desired. The catheter body 12 is flexible, i.e., bendable, but substantially non-compressible along its length. The catheter body 12 can be of any suitable construction and made of any suitable material. One construction comprises an outer wall 20 made of polyurethane or PEBAX. Alternatively, the outer wall 20 is made of a suitable silicone, silicone-based, or silicone-containing material. The outer wall 20 can comprise an embedded braided mesh of stainless steel or the like to increase torsional stiffness of the catheter body 12 so that when the control handle 16 is rotated, the intermediate section 14 rotates in a corresponding manner.

The overall length and diameter of the catheter 10 may vary as desired. One exemplary catheter has an overall length of about 24 inches. The outer diameter of the catheter body 12 is not critical, but should be no more than about 15 french or smaller. The inner surface of the outer wall 20 may be lined with a stiffening tube 22, which can be made of any suitable material, for example nylon or polyimide. The stiffening tube 22, along with the braided outer wall 20, provides improved torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. One exemplary catheter has an outer diameter of about 0.092 inch and a lumen diameter of about 0.052 inch.

Figure 2A:
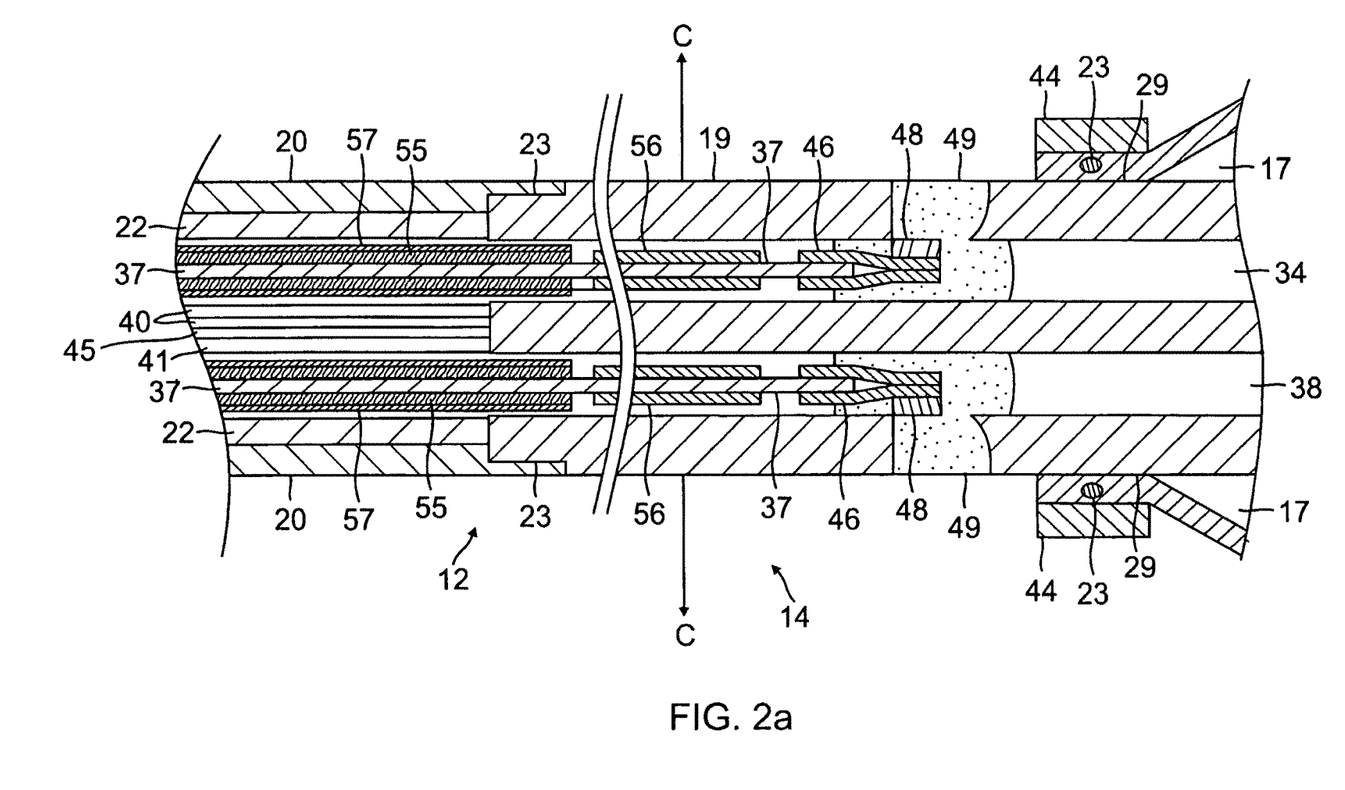
FIG. 2a is a side cross-sectional view of an embodiment of a catheter of the present invention, including a junction of a catheter body and an intermediate section, taken along a diameter.
Figure 2B:
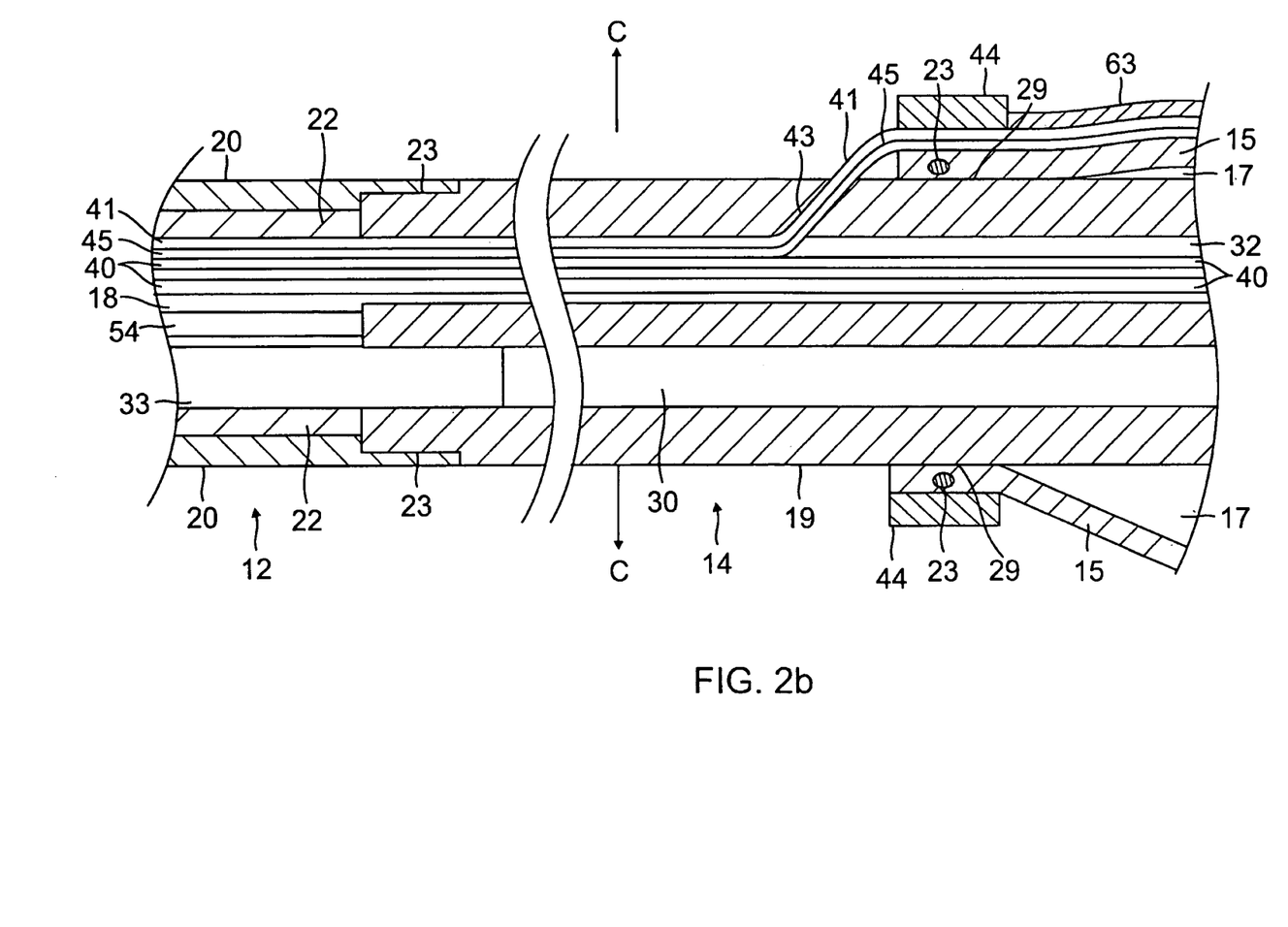
FIG. 2b is a side cross-sectional view of an embodiment of a catheter of the present invention, including a junction of a catheter body and an intermediate section, taken along another diameter.
Figure 2C:
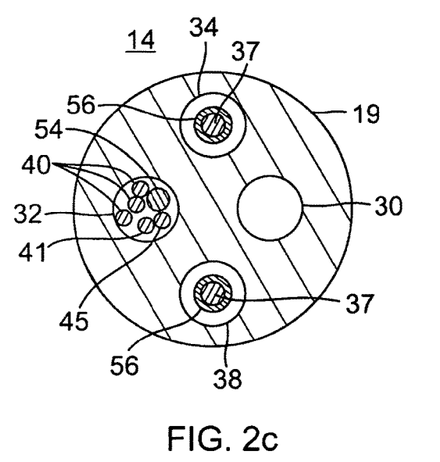
FIG. 2c is an end cross-sectional view of the intermediate section of FIGS. 2a and 2b, taken along line c-c.

As shown in the embodiment of FIGS. 2a, 2b and 2c, the intermediate section 14 comprises a shorter section of tubing 19 having at least four lumens 30, 32, 34 and 38. The tubing 19 is made of a suitable non-toxic material and can be more flexible than the catheter body 12. A nonlimiting example of a suitable material for the tubing 19 is braided polyurethane, i.e., polyurethane with an embedded braided mesh of stainless steel or the like. Alternatively, the tubing 19 is made of a suitable silicon, silicone-based or silicone-containing material. The tubing 19 may have a length ranging between about 1.0 inches and 5.0 inches, preferably about 1.25 inches and 3.0 inches, and more preferably about 1.5 inches and 2.5 inches.

The outer diameter of the intermediate section 14, like that of the catheter body 12, should be no greater than about 12 french. The lumens 30, 32, 34 and 38 each have a diameter ranging from about 0.018 to about 0.058 inch depending on the french size of the catheter body.

One means for attaching the catheter body 12 to the intermediate section 14 is illustrated in FIGS. 2a and 2b. The proximal end of the intermediate section 14 comprises an outer circumferential notch 23 that receives the inner surface of the outer wall 20 of the catheter body 12. The intermediate section 14 and catheter body 12 are attached by glue or the like.

Figure 3A:
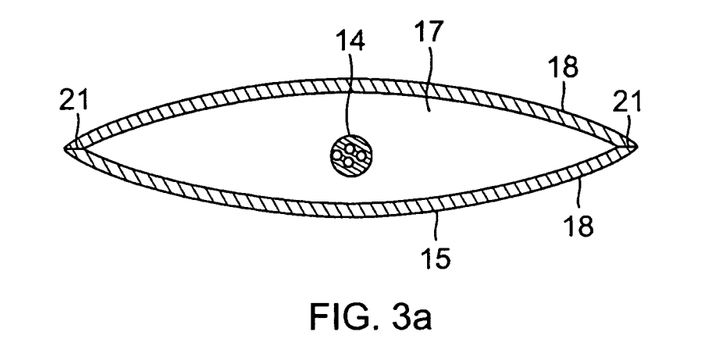
FIG. 3a is an end cross-sectional view of an embodiment of an inflated barrier member.
Figure 3B:
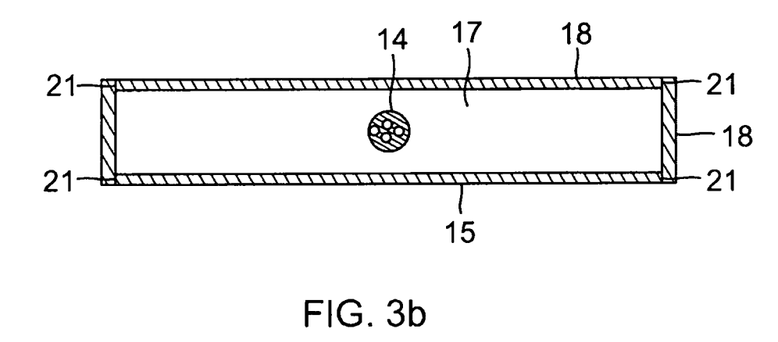
FIG. 3b is an end cross-sectional view of another embodiment of an inflated barrier member.
Figure 3C:
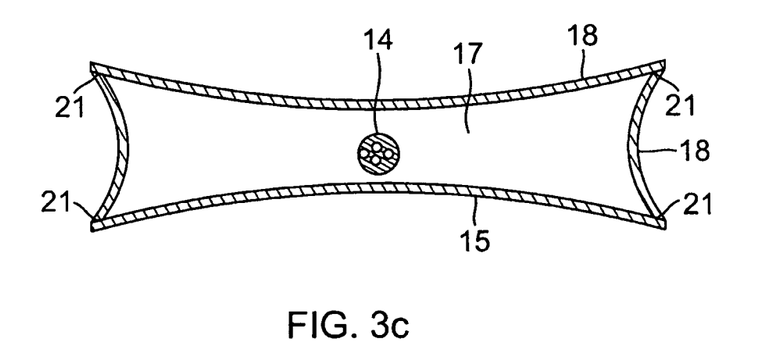
FIG. 3c is an end cross-sectional view of yet another embodiment of an inflated barrier member.

In accordance with a feature of the invention, an inflatable barrier member 15, or balloon member, is mounted on a distal portion of the intermediate section 14. As shown in FIGS. 3a-3c, the barrier member 15 has an interior cavity 17 that is fluid-tight to contain liquids, such as saline solution or other bio-compatible fluids (liquid or gas, e.g., carbon dioxide). When inflated, the barrier member 15 assumes a configuration that can protect organs or tissue in the patient's body. When deflated, the barrier member 15 can be relocated in or removed from the patient's body.

Figure 4A:
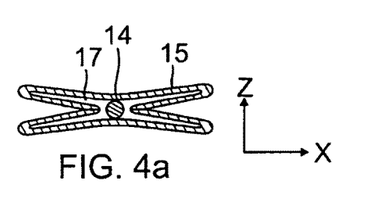
FIG. 4a is an end cross-sectional view of an embodiment of a deflated barrier member.
Figure 4B:
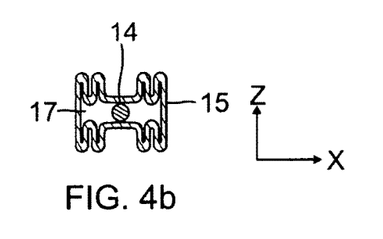
FIG. 4b is an end cross-sectional view of another embodiment of a deflated barrier member.
Figure 4C:
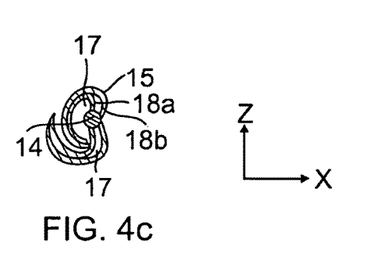
FIG. 4c is an end cross-sectional view of yet another embodiment of a deflated barrier member.
Figure 4D:
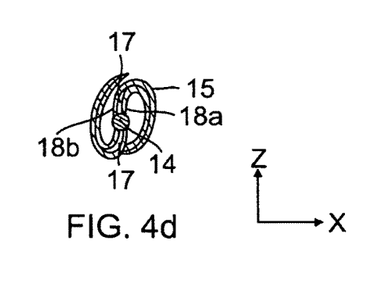
FIG. 4d is an end cross-sectional view of an embodiment of a deflated barrier member.

The barrier member 15 can be constructed of a variety of suitable bio-compatible materials, elastic or nonelastic, including polyvinyl chloride (PVC), cross-linked polyethylene (PE), polyethylene terephthalate (PET), nylon, and combinations thereof. Depending on the configuration and manufacturing methods, the barrier member 15 can have a seamless design, as through extrusion, or be made of multiple panels 18 whose outer edges are bonded by heat, stitching and/or adhesive. Collapsed or deflated configurations, including those of FIGS. 4a-4d can be facilitated by means of darts, cutouts, inserts, pleats, preformed creases and/or folds strategically provided in the construction material, as understood by one of ordinary skill in the art. Moreover, a panel 18a can have a smaller and/or a slightly offset configuration than an opposing panel 18b to facilitate a coil or spiral configuration, such as shown in FIGS. 4c and 4d.

The size of the interior cavity 17 increases and decreases upon inflation and deflation of the barrier member 15. Upon inflation, the interior cavity 17 increases which expands the barrier member into a deployed configuration. In that regard, the barrier member in the deployed configuration can have a generally uniform thickness (FIG. 3b) or it may have a nonuniform thickness (FIGS. 3a and 3c). In either case, the barrier member 15 in the deployed configuration extends significantly at least along two dimensions (e.g., x and y in FIGS. 5a-5c) relative to a third dimension (e.g., z in FIG. 4d) to provide a relatively large surface that can be interposed between the esophagus and the heart.

Figure 5A:
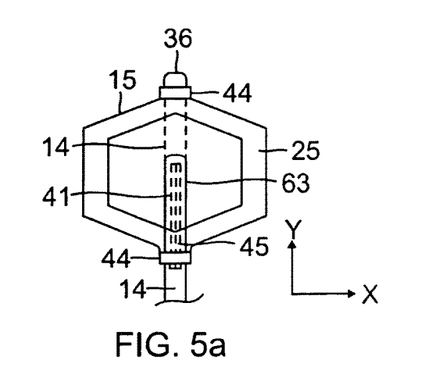
FIG. 5a is a top view of an embodiment of an inflated barrier member, with a thermocouple temperature sensor.
Figure 5B:
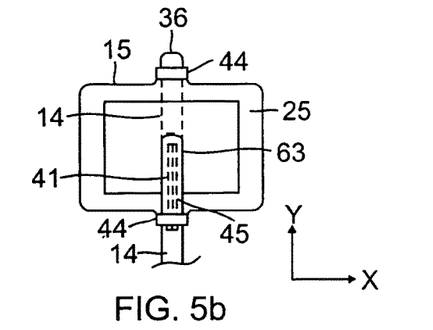
FIG. 5b is a top view of an embodiment of another inflated barrier member, with a thermocouple temperature sensor.
Figure 5C:
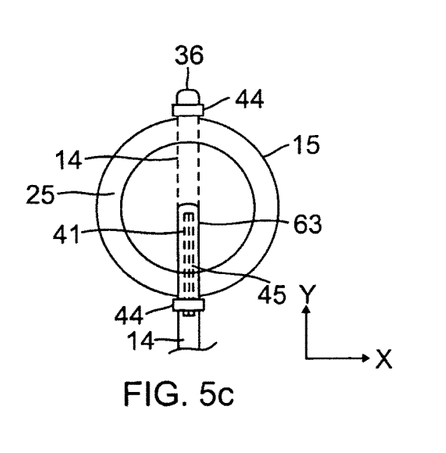
FIG. 5c is a top view of an embodiment of yet another inflated barrier member, with a thermocouple temperature sensor.

With reference to FIGS. 5a-5c, the large surface can take on a variety of predetermined configurations, including, a polygonal (e.g., a hexagonal shape and a rectangular shape) and a circular shape. When inflated, the barrier member 15 has dimensions ranging between about 1.0 inch×1.0 inch× 0.125 inch and 7.0 inches×7.0 inches×1.0 inch., and more preferably, 4.0 inches.×4.0 inches.×0.25 inch.

When deflated, the barrier member 15 can collapsed into a variety of predetermined configurations as shown in FIGS. 4a-4d. The barrier member is adapted to minimize its size and/or cross-section so as to facilitate insertion, positioning, repositioning and/or removal of the catheter. These collapsed configurations may have a cross-sectional configuration of pleats or a bow-tie, an accordion, a coil or a spiral.

Shape-memory elements 23, such as thin nitinol wires, can be embedded in the barrier member 15 to facilitate retraction of the barrier member into the collapse configuration when the barrier member is deflated. The shape-memory elements can bias the barrier member to collapse in a predetermined manner and into a predetermined shape. Moreover, shape-memory elements 23 can also bias the barrier member to adopt a predetermined deployed configuration. Certain predetermined curvatures or cross sections may better stabilize the barrier member against the esophagus and/or the heart.

Radiopaque materials 25, for example, barium can be embedded, printed or applied to the construction material to render the barrier member visible or otherwise detectable under fluoroscopy or X-ray for guiding and positioning the barrier member within the patient's body. The radiopaque material can be applied in a predetermined manner, for example, to outer edges of the barrier member 15. Radiopaque materials can also be introduced in the fluid that is used to inflate the barrier member. Suitable fluid can be loaded with bismuth trioxide, tungsten and/or other radiopaque filler.

The barrier member 15 has a distal opening 27 and a proximal opening 29 through which a distal portion of the intermediate section 14 extends. The distal portion traverses the interior cavity 17 of the barrier member. The openings 27 and 29 are sealed against the tubing 19 of the intermediate section 14 by means of rings 44 and/or adhesives so that the barrier member is fluid-tight at the openings 27 and 29 and the barrier member is fixedly mounted on the intermediate section 14. As understood by one of ordinary skill in the art, the rings 44 may be adapted for electrophysiologic functions such as ablation, pacing and/or mapping. The rings may also comprise radiopaque materials.

In the illustrated embodiment, the lumen 30 of the tubing 19 of the intermediate section 14 is dedicated to transporting fluid, e.g., saline, to and from the barrier member 15. One or more ports 35 are formed in the tubing 19 allowing communication between the lumen 30 and the interior cavity 17 of the barrier member. Thus, fluid is able to flow through ports 35 to inflate or deflate the barrier member.

Figure 7:
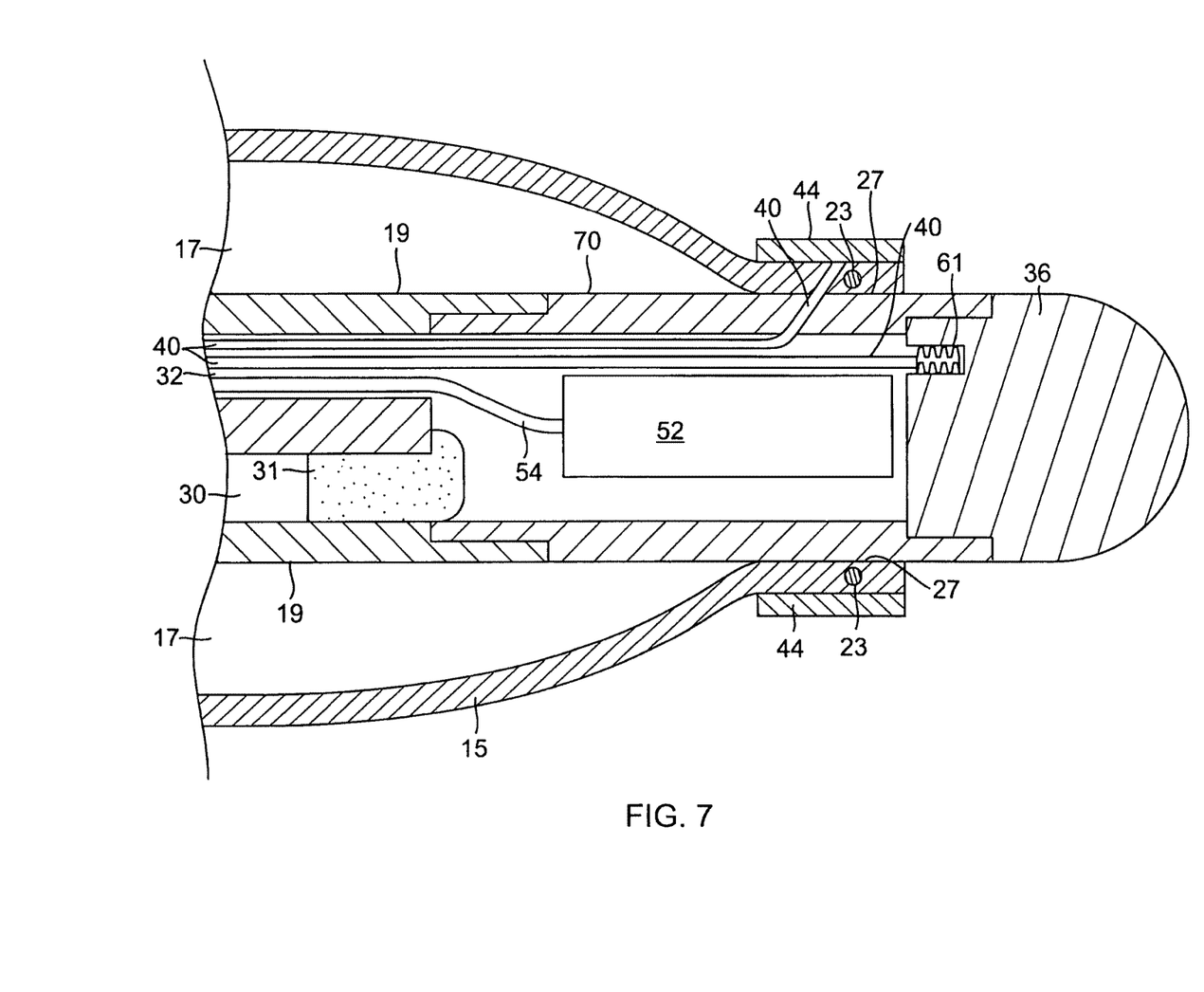
FIG. 7 is a side cross-sectional view of an embodiment of a catheter of the present invention, including a distal end.
Figure 8:
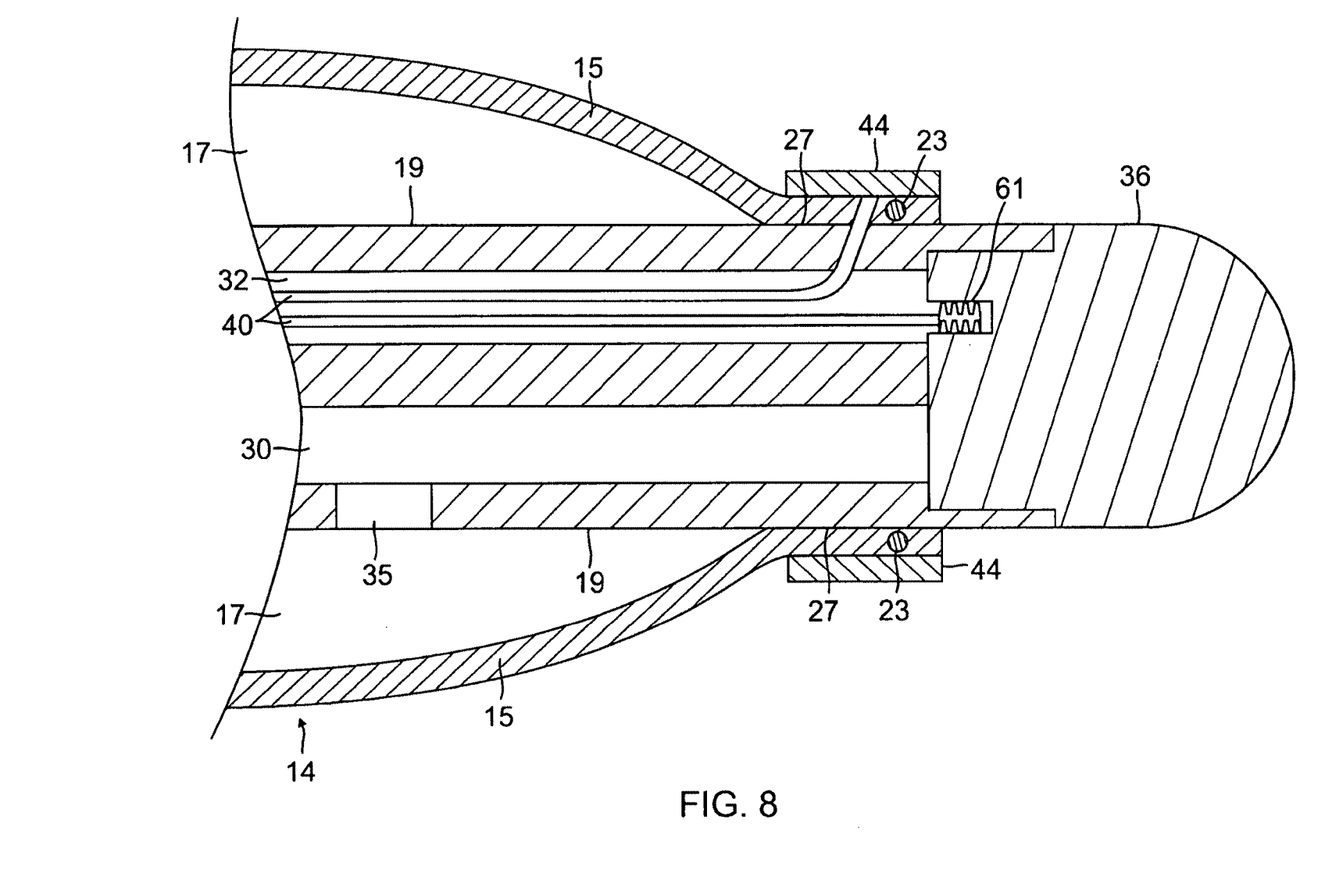
FIG. 8 is a side cross-sectional view of another embodiment of a catheter of the present invention, including a distal end.

In the illustrated embodiment of FIG. 7, the lumen 30 at its distal end is sealed with plug 31 of glue or adhesive. The proximal end of lumen 30 is in communication with a fluid tube 33 that extends into the lumen 30 from the central lumen 18 of the catheter shaft 12 and terminates in a proximal portion of the intermediate section. The distal end of the fluid tube 33 is anchored in the lumen 30 of the intermediate section 14 by polyurethane glue or the like. The fluid tube 33 extends through the central lumen 18 of the catheter shaft 12 and through the control handle 16 and terminates in a luer hub 47 or the like at a location proximal to the control handle. The fluid introduced thereby through the hub 47, the tube 33 and the ports 35 into the barrier member 15 is preferably a biologically compatible fluid, and may be in a gaseous or liquid state. Suitable fluids include saline, water, carbon dioxide, nitrogen, and helium.

The rate of fluid flow through the catheter 10 may be controlled by any suitable fluid infusion pump or by pressure. A suitable infusion pump is the FLOGARD™ available from Baxter. The rate of fluid flow through the catheter preferably ranges from about 17 ml/min to about 50 ml/min, more preferably from about 25 ml/min to about 30 ml/min. Preferably the fluid is maintained at about room temperature. As understood by one of ordinary skill in the art, the pump is also adapted to draw fluid from the barrier member 15 so as to deflate the barrier member in preparation for relocating or removing the catheter from the patient's body.

Distal of the intermediate section 14 is a dome tip 36 to provide the catheter with an atraumatic distal end. The dome tip 36 can be formed from polyurethane or a molded or formed plastic tip. In the illustrated embodiment, the dome tip is a tip electrode and a lead wire 40 is provided with its distal end terminating in a blind hole 61 in a proximal end of the tip electrode. The lead wire is adapted to transmit electrical signals or energy for mapping and/or ablation. Moreover, the rings 44 securing the barrier member 15 to the intermediate section 14 may comprise ring electrodes with lead wires 40 that can also transmit electrical signals and energy for mapping and ablation. Both the tip electrode and/or the ring electrodes may also be used to measure the proximity of another catheter with in the vicinity of the catheter 10. This proximity may be measured by any suitable technique, such as impedance, inductance, capacitance, pacing, or location in a magnetic field, as is understood by one of ordinary skill in the art. Furthermore, the tip electrode and/or ring electrodes may be used as either a source or ground electrode for bi-polar ablation with another catheter located within the interior chamber of the heart.

Each lead wire 40 is connected at its distal end to its corresponding ring electrode 44 by any suitable technique. Each lead wire 50 can be connected to its corresponding ring electrode 27 by first making a small hole through the tubing 19. Such a hole can be created, for example, by inserting a needle through the tubing and heating the needle sufficiently to form a permanent hole. A lead wire is then drawn through the hole by using a microhook or the like. The end of the lead wire is then stripped of any coating and welded to the underside of the ring electrode 44, which is then slid into position over the hole and fixed in place with polyurethane glue or the like. Lead wire 40 to ring electrode 27 contact may also be achieved by means of soldering or pressure contact resulting from crimping of the electrode.

The lead wires 40 for the tip electrode 36 and the ring electrodes 44 extend through the lumen 32 of the intermediate section 14, through the central lumen 18 of the catheter body 12, through the control handle 16, and terminate at their proximal end in an input jack 51 that may be plugged into an appropriate monitor (not shown). Portions of the wires extending through the catheter body 12 may be encased within a protective sheath. The protective sheath can be made of any suitable material, for example polyimide. The protective sheath is anchored at its distal end to the side wall of the catheter body by gluing it to the side wall with polyurethane glue or the like.

In the illustrated embodiment, the intermediate section 14 is deflectable in two directions within a plane. As shown in FIGS. 2a and 2c, the catheter 10 comprises a pair of puller wires 37 that extend from the control handle 16, through the central lumen 18 in the catheter body 12, and into a respective lumens 34 and 38 of the tubing 19 of the intermediate section 14. As understood by one of ordinary skill in the art, the proximal ends of the puller wires are anchored within the control handle 16 which is adapted to allow user manipulation of the puller wires for deflecting the intermediate section. Although the distal ends of the puller wires can be anchored at any position along the catheter, the distal ends of the puller wires 37 of the illustrated embodiment are anchored at location(s) proximal the distal end of the barrier member 15 so as to minimize interference between the deflection of the intermediate section 14 and the barrier member 15 mounted thereon. Each distal end of the puller wire 37 is anchored to a side wall of the tubing 19 and attached by means of an anchor 44 fixedly attached to the distal end of the puller wire 32. The anchor 44 is formed by a metal tube 46, e.g., a short segment of hypodermic stock, that is fixedly attached, e.g. by crimping, to the distal end of a puller wire 37. The tube has a section that extends a short distance beyond the distal end of the puller wire 37. A cross-piece 48 made of a small section of stainless steel ribbon or the like is soldered or welded in a transverse arrangement to the distal end of the metal tube which is flattened during the operation. This creates a T-bar anchor. A notch 49 is created in the side of the tubing 19, resulting in an opening in each of the off-axis lumens 34 and 38 carrying the puller wires 37. The cross piece 48 lies transversely within the notch. The notch is then sealed with polyurethane glue or the like to give a smooth outer surface. The glue flows into the off-axis lumens 334 and 38 to fully secure the anchor 44. Other means for anchoring the puller wires 37 would be recognized by those skilled in the art and are included within the scope of the invention. The puller wires are made of any suitable metal, such as stainless steel or Nitinol.

The catheter 10 may further comprise compression coils 55 in surrounding relation to each puller wire 37. Each compression coil 55 is made of any suitable metal, such as stainless steel. Each compression coil 55 is tightly wound on itself to provide flexibility, i.e., bending, but to resist compression. The inner diameter of compression coil 55 is slightly larger than the diameter of the puller wire. A coating, such as Teflon® or the like on the puller wires allows them to slide freely within the compression coils 55. The outer surface of the compression coils 55 can be covered along most of its length by a flexible, non-conductive sheath 57 to prevent contact between the compression coil 55 and any wires or cables also dispersed within the central lumen 18 of the catheter body 12. A nonlimiting example of a suitable material for the non-conductive sheath 62 is polyimide tubing.

Each compression coil 55 is anchored at its proximal end to the proximal end of the stiffening tube 22 of the catheter body 12 by a proximal glue joint. When a stiffening tube is not used, each compression coil is anchored directly to the outer wall 20 of the catheter body 12. The compression coil 55 is anchored at its distal end to the proximal end of the intermediate section 14 by distal glue joint. Alternatively, the distal end of each compression coil may be anchored to the distal end of the stiffening tube 22 or the distal end of the outer body 20 (when no stiffening tube is used).

Within the off-axis lumens 34 and 38, each puller wire 37 is surrounded by a plastic sheath 56, preferably made of Teflon® The plastic sheathes 56 prevent the puller wires 37 from cutting into the wall of the tubing 19 of the intermediate section 14 when deflected. Each sheath 56 ends near the distal end of each puller wire 37. Alternatively, each puller wire 37 can be surrounded by a compression coil where the turns are expanded longitudinally, relative to the compression coils extending through the catheter body, such that the surrounding compression coil is both bendable and compressible.

Longitudinal movement of a puller wire 37 in the proximal direction relative to the catheter body 12 by means of user manipulation of the control handle results in deflection of the intermediate section 14 (with the barrier member 15 and tip electrode 36 mounted thereon) in the direction of the lumen containing that puller wire. Deflection occurs between the distal end of the compression coil 55 surrounding the puller wire and the distal anchor site of that puller wire. A suitable bidirectional control handle for use in the present invention is described in copending application Ser. No. 09/822,087, filed Mar. 30, 2001 and entitled "Steerable Catheter with a Control Handle Having a Pulley Mechanism", the disclosure of which is incorporated herein by reference. Other suitable bidirectional control handles are described in U.S. Pat. Nos. 6,123,699, 6,171,277, 6,183,463, and 6,198,974, the disclosures of which are incorporated herein by reference.

Figure 2D:
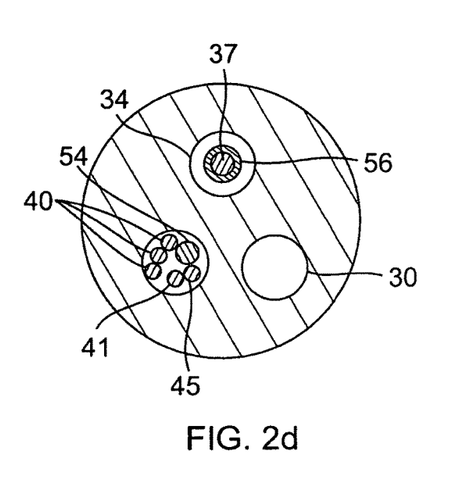
FIG. 2d is an end cross-sectional view of an intermediate section of another embodiment of a catheter of the present invention.
Figure 2E:
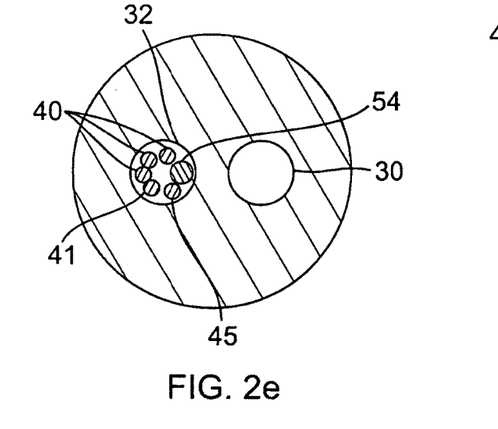
FIG. 2e is an end cross-sectional view of an intermediate section of yet another embodiment of a catheter of the present invention.

Although the above embodiment is described as including two puller wires for bi-directional control of the intermediate section 14, it is understood by one of ordinary skill in the art that that one puller wire can alternatively be used for uni-directional catheter (FIG. 2d) or none at all for a nondirectional catheter (FIG. 2e). Nonlimiting examples of suitable control handles 16 for use in the present invention are disclosed in U.S. Pat. Nos. 6,198,974 and 6,468,260, the entire disclosures of which are incorporated herein by reference.

A temperature sensing means is provided on the barrier member 15 of the illustrated embodiment of the catheter 10. Any conventional temperature sensing means, e.g., a thermocouple or thermistor, may be used. With reference to FIGS. 2b, 5a-5c, a thermocouple formed by a wire pair is mounted on the barrier member 15 to detect temperature from atrial procedures that may adversely affect the esophagus. One wire of the wire pair is a copper wire 41, e.g., a number 40 copper wire. The other wire of the wire pair is a constantan wire 45, which gives support and strength to the wire pair. The wires 41 and 45 of the wire pair are electrically isolated from each other except at their distal ends where they contact and are twisted together, covered with a plastic tubing (not shown) e.g., polyimide, and further with epoxy. The plastic tubing, and the wires 41 and 15 are then attached by a coating 63 of polyurethane glue or the like to an outer surface of the barrier member 15. The wires 41 and 45 extend through a hole 43 formed in the outer wall of the tubing 19, through the lumen 32 of the intermediate section 14, and through the central lumen 18 of the catheter body 12. Within the catheter body 12, the wires 41 and 45 may extend through the protective sheath that isolates the wires from other wires or cables. The wires 41 and 45 extend out through the control handle 16 and to connector 51 connectable to a temperature monitor (not shown).

Figure 9:
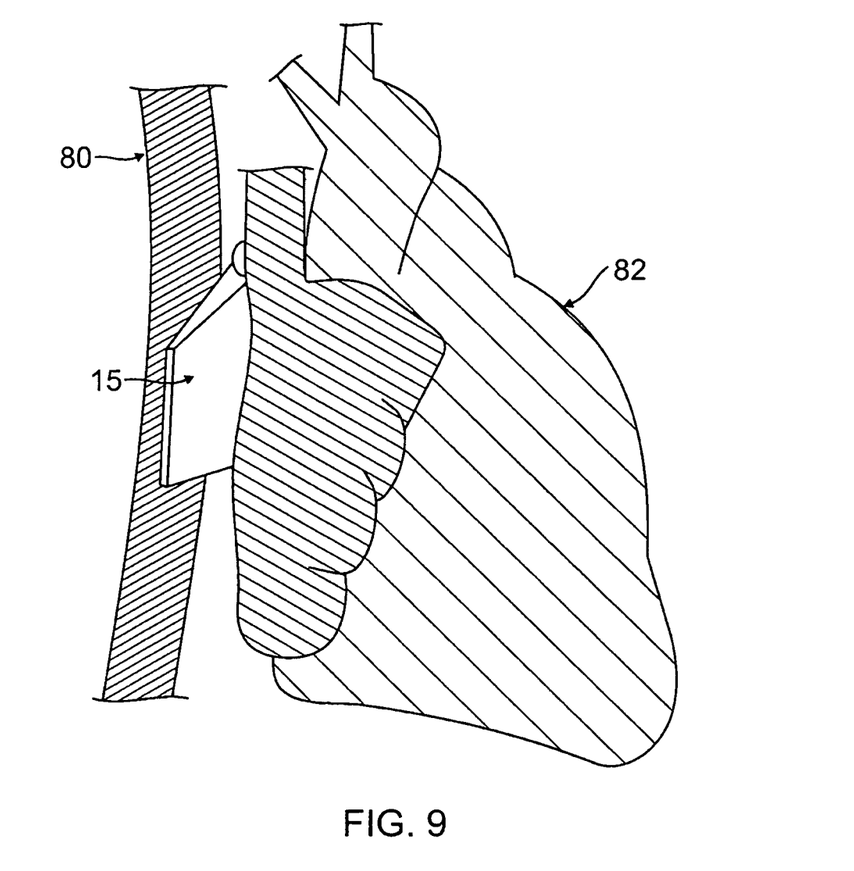
FIG. 9 is a representation of a catheter of the present invention in use as a barrier between a heart and an esophagus.

The illustrated embodiment includes an electromagnetic location sensor 52 that is housed immediately proximal the dome tip 36. As illustrated in FIG. 7, the sensor 52 is housed in a short section of tubing 70 extending between the distal end of the tubing 19 of the intermediate section 14 and the dome tip 36. The electromagnetic sensor 52 is anchored to the side wall of the tubing 70 by any suitable means, e.g., by polyurethane glue or the like. The electromagnetic sensor 52 may be used to locate the tip electrode 31 and the distal edge of the barrier member 15 to ensure that the barrier member 15 is properly positioned, for example, between esophagus 80 and heart 82 (FIG. 9).

The electromagnetic sensor 52 is connected to an electromagnetic sensor cable 54, which extends through the lumen 32 of the intermediate section 14, through the central lumen 18 of the catheter body 12, and into the control handle 16. The electromagnetic sensor cable 54 comprises multiple wires encased within a plastic covered sheath. The electromagnetic sensor cable 54 extends out the proximal end of the control handle 16 within an umbilical cord 59 to a sensor control module (not shown) that houses a circuit board (not shown). The circuit board amplifies the signal received from the electromagnetic sensor 74 and transmits it to a computer in a form understandable by the computer. Suitable electromagnetic sensors for use with the present invention are described, for example, in U.S. Pat. Nos. 5,558,091, 5,443,489, 5,480,422, 5,546,951 and 5,391,199, the entire disclosures of which are incorporated herein by reference.

With reference to FIG. 5, an alternative embodiment of a distal end of the catheter 10 without an electromagnetic location sensor is illustrated. In this embodiment, the tip electrode 36 is attached directly to the distal end of the tubing 19 of the intermediate section 19, such that the tip electrode seals the lumen 30 through which fluid is delivered to and from the barrier member 15.

Figure 10A:
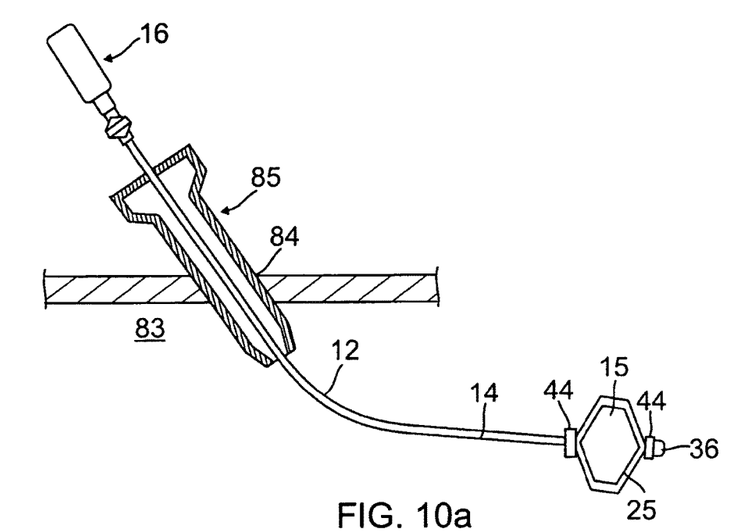
FIG. 10a illustrates a catheter of the present invention in use with a trocar.
Figure 10B:
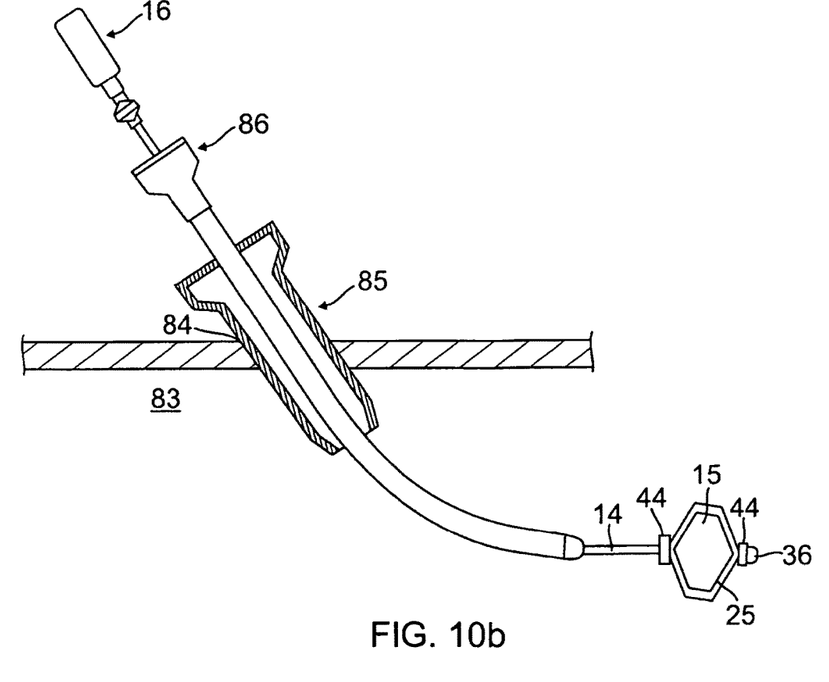
FIG. 10b illustrates a catheter of the present invention in use with a guiding sheath and a trocar.

In use, the catheter 10 is inserted into the chest cavity or the abdominal cavity of the patient with the barrier member 15 in any of the collapsed or stored configurations. A trocar 85 providing a port 84 into the patient's body, e.g., the chest cavity 83, may be used with or without a delivery device 86, such as a guiding sheath, as shown in FIGS. 10a and 10b. The radiopaque material 25 embedded in the barrier member and/or the radiopaque material of the tip electrode 36 and ring electrodes provides a visual reference of the location of the barrier member 15 as the barrier member is guided to the esophagus and positioned between the esophagus and the heart to shield the anterior wall of the esophagus during ablation or other electrophysiologic procedures performed on the left atrium, including the posterior wall of the left atrium.

Before such procedures are performed on the heart, the barrier member 15 is extended past the distal end of the guiding sheath 86 and fluid is delivered to the barrier member 15 via the tubing 33, the lumen 30 and the ports 35. As the fluid fills the barrier member, it expands and assumes a deployed configuration that provides a large surface barrier between the esophagus and the heart. It is understood that the barrier member can also be inflated before it is positioned.

The radiopaque material 25 provided at the outer edges of the barrier member 15 can provide visual reference of the degree of inflation and/or when sufficient deployment and expansion have been attained. Deflection of the intermediate section 14 as accomplished by user manipulation of the control handle 16 can be performed at any time to maneuver the barrier member 15 as desired. It is understood by one of ordinary skill in the art that the barrier member 15 can also be placed in direct contact with the esophagus such that deflection of the intermediate section and hence the barrier member physically shifts or repositions the esophagus, or at least the wall of esophagus in contact with the barrier member, away from the heart.

Figure 11:
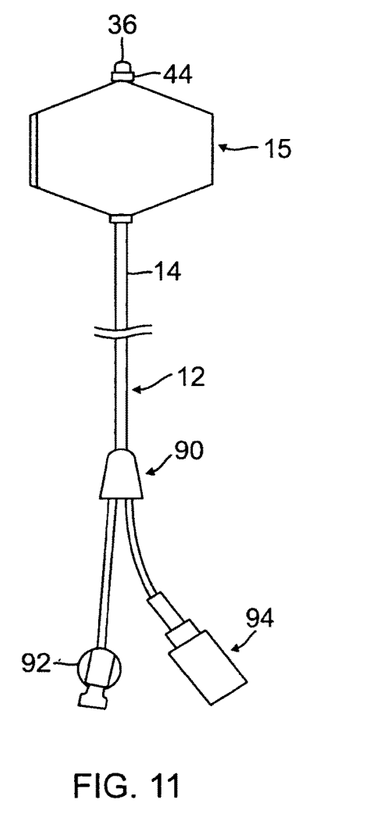
FIG. 11 illustrates a catheter of the present invention standing alone.
Figure 12:
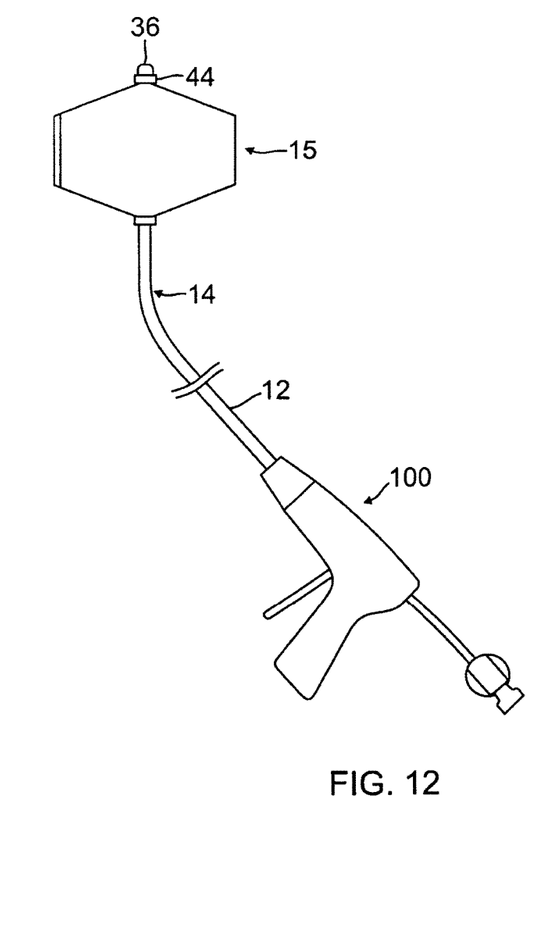
FIG. 12 illustrates a catheter of the present invention adapted for laproscopic use

It is understood by one of ordinary skill in the art that additional different embodiments are contemplated in the present invention, including an embodiment of the catheter that does not employ a control handle but rather a side port with luer hub 92 and an electrical connector 94 that both are connected to the catheter shaft by means of a junction 95 (see FIG. 11). Alternatively, the catheter may employs a handle 100 adapted for laproscopic procedures.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A device adapted to protectively shield an esophagus within a chest cavity of a patient, comprising:

a catheter body;

a distal section distal the catheter body;

a barrier member affixed to the distal section, wherein the barrier member is configured to adopt an expanded configuration when inflated with a fluid and a collapsed configuration when deflated, wherein the barrier member in the expanded configuration includes x, y and z dimensions in a Cartesian coordinate system, the z dimension being a thickness dimension of the barrier member in the expanded configuration, and each of the x and y dimensions being larger than the z dimension such that in the expanded configuration the x and y dimensions define a generally planar configuration having two opposing generally flat and continuous surfaces, and the generally planar configuration is configured to fit between a heart and the esophagus within the chest cavity to provide a protective shield for the esophagus from procedures performed on the heart within the chest cavity; and at least one shape memory wire comprising a shape memory material embedded in the barrier member configured to bias the barrier member to expand or collapse to a predetermined configuration.

2. A device of claim 1, wherein the barrier member is a balloon.

3. A device of claim 1, wherein the x and y dimensions of the barrier member define a rectangular shape in the expanded configuration.

4. A device of claim 1, wherein the x and y dimensions of the barrier member define a circular shape in the expanded configuration.

5. A device of claim 1, wherein the x and y dimensions of the barrier member define a polygonal shape in the expanded configuration.

6. A device of claim 1, wherein the barrier member has folds in the collapsed configuration.

7. A device of claim 1, wherein the barrier member has a spiral shape in the collapsed configuration.

8. A device of claim 1, wherein the at least one shape-memory wire is configured to bias the barrier member to adopt a predetermined shape in the collapsed configuration.

9. A device of claim 1, wherein the at least one shape memory wire is configured to bias the barrier member to adopt a predetermined shape in the expanded configuration.

10. A device of claim 1, wherein the distal section is deflectable.

11. A device of claim 10, further comprising a control handle adapted to enable user manipulation for deflecting the distal section.

12. A device of claim 1, wherein the barrier member contains a radiopaque material.

13. A device of claim 1, wherein the distal section has at least one lumen for delivering fluid to and from the barrier member.

14. A device of claim 13, wherein the distal section has another lumen through which a puller wire extends for deflecting the distal section.

15. A device of claim 1, wherein the distal section includes a tip electrode.

16. A device of claim 1, wherein the distal section extends through the barrier member.

17. A device of claim 1, wherein the distal section includes rings affixing the barrier member to the distal section.

18. A device of claim 17, wherein the rings include ring electrodes.

19. A device of claim 18, wherein the rings comprise internal reference electrodes.

20. A device of claim 18, wherein the rings comprise bi-polar electrodes adapted for bi-polar ablation.

21. A device of claim 18, wherein the rings comprise electrodes adapted for generating electrogram data from an exterior surface of the heart.

22. A device of claim 1, further comprising an electromagnetic location sensor mounted in the distal section.

23. A device of claim 1, wherein the fluid contains radiopaque material.

* * * * *